United States Patent [19]
DePierro et al.

[11] Patent Number: 5,938,673
[45] Date of Patent: Aug. 17, 1999

[54] TONGUE CLEANING DEVICE

[75] Inventors: Karen DePierro, Piscataway; Susan Greenfeder, Metuchen; Lisa Christina-Beck, Burlington; John Curtis, Bloomsbury, all of N.J.

[73] Assignee: Colgate-Palmolive Company, New York, N.Y.

[21] Appl. No.: 09/078,773

[22] Filed: May 14, 1998

[51] Int. Cl.⁶ .............................. A61B 17/24; A61F 9/00
[52] U.S. Cl. .................................................. 606/161
[58] Field of Search ..................... 606/161, 162, 606/160

[56] References Cited

U.S. PATENT DOCUMENTS

| | | |
|---|---|---|
| 1,179,426 | 4/1916 | Hamilton . |
| 2,599,191 | 6/1952 | Meunier . |
| 3,943,592 | 3/1976 | Bhaskar . |
| 5,678,273 | 10/1997 | Porcelli . |
| 5,715,850 | 2/1998 | Markgraaff .............................. 606/162 |
| 5,792,159 | 8/1998 | Amin ...................................... 606/161 |

*Primary Examiner*—Michael Buiz
*Assistant Examiner*—Vy Q. Bui
*Attorney, Agent, or Firm*—Henry S. Goldfine

[57] ABSTRACT

A tongue cleaner or scraper, of an absorbent, flexible, loop pile which conforms to the surface of the tongue and which improves cleaning effectiveness, while providing a soft, consumer acceptable tongue feel.

14 Claims, 2 Drawing Sheets

TONGUE CLEANING DEVICE

BACKGROUND OF THE INVENTION

1. Field of the Invention

The present invention relates to a tongue cleaner or scraper, and more particularly to a tongue cleaner formed of a soft, absorbent, flexible, polymeric loop pile to improve cleaning effectiveness and consumer acceptability.

2. The Prior Art

Mouth odors are related to dead cells in the mouth, trapped and decaying food particles and microorganisms such as bacteria, either alive or dead. These things remain in the mouth, unless removed, will mix with saliva to form plaque, a white slimy substance. Such plaque which coats the oral surfaces not only contributes to bad breath, but is also harmful to the teeth and gums.

The physiology of the tongue is slightly fury in texture, with numerous projections, i.e. papillae, that entrain dead cells, decaying food particles, bacteria and plaque, becoming a wet breeding ground for bacteria to grow. Daily tongue cleaning through scraping, removes debris from the tongue and significantly reduces bacteria and plaque-coating without causing any deleterious tissue changes to the tongue. U.S. Pat. No. 5,217,475 further discloses that such tongue cleaning significantly inhibits plaque formation on the teeth, and appreciably reduces the level of bacteria in the mouth to reduce mouth odor.

The background art discloses many types of tongue cleaning devices, these devices typically employing rigid, nonabsorbent arcuate i.e. sickle like, or straight blades to remove debris from the tongue, by a scraping action with the blade across the surface thereof. Such rigid, nonabsorbent blade devices are disclosed in U.S. Pat. Nos. 3,477,435; 3,890,964, 4,455,704 and 5,569,278. U.S. Pat. No. 5,217,475 discloses a similar nonabsorbent, disposable tongue scraper, formed of flexible material bent along its length, with each end held in opposing prongs of a forked handle, and wherein the edge of the scraper that is adapted to scrape the tongue is serrated. As demonstrated herein, the nonabsorbent and relatively rigid devices disclosed in the aforementioned U.S. Patents, lack the ability to effectively remove wet bacteria and plaque on the surface of the tongue. Further, the disclosed blades, either straight, arcuate or serrated are uniformly, relatively rigid and impart a harsh feel when applied to the tongue, a feel which is not consumer acceptable.

U.S. Pat. No. 3,943,592 discloses a tongue brushing device comprised of a tape attached to one end of a flattened, elongated member having a vertical profile of 3mm; wherein, the tape contains a high density of flexible nylon fiber hooks. The nylon fiber hooks are in alternate directions to remove cellular debris and the like from the tongue, as the tongue brushing device is applied to the tongue in alternate forward and backward motions. The nylon fiber hooks are formed by precision cutting, in alternate directions, of a woven series of raised and staggered high density loops. The nylon fiber hooks provided within U.S. Pat. No. 3,943,592 form a brush which enhances the removal of debris and plaque from the tongue. However, as demonstrated herein, the use of hooks, as disclosed in U.S. Pat. No. 3,943,592, does not provide the most effective configuration necessary to absorb and effectively remove the wet debris, bacteria and plaque accumulation from the tongue. Further, hooks as disclosed within U.S. Pat. No. 3,943,592 have an inherently harsh and scratchy feel.

There is a need in the art for a more effective tongue cleaning device to improve the absorption, accumulation and removal of the wet debris, bacteria and plaque from the tongue, while providing a tongue feel that is consumer acceptable.

SUMMARY OF THE INVENTION

The invention is a soft, absorbent, effective tongue cleaning device which conforms to the surface of the tongue, comprising an elongated member having at one end a handle for gripping the tongue cleaning device and at the other end a flattened head portion to which a backing tape is attached, the backing tape containing a plurality of flexible multifilament yarn bundles which form a loop pile.

The multifilament yarn bundles are woven or otherwise attached to the backing tape. There are from about 120 to about 160 bundles per square cm of the backing tape, each bundle containing a plurality of soft, flexible, polymeric monofilament loops, each monofilament therein being from about 0.03 to about 0.045 mm in diameter; the monofilament loops forming a dense, absorbent pile, the pile extending from about 0.7 mm to about 1.4 mm in height above the backing tape. The end of the elongated member opposite that of the flattened head portion, which forms the handle for gripping the tongue cleaning device, may be flat, generally cylindrical, or contoured to provide ease in holding. The handle may be raised at an angle of from 5 to 20 degrees from the plane of the flattened head portion to facilitate cleaning the downward curving posterior portion of the tongue.

As will be further demonstrated, the soft, absorbent, flexible polymeric monofilament loops which form the pile head of the present invention, absorbs and accumulates unexpected and significant quantities of wet debris, bacteria and plaque when applied to the surface of the tongue; while imparting a soft, consumer acceptable, tongue feel during use thereon.

BRIEF DESCRIPTION OF THE DRAWINGS

For a fuller understanding of the nature of the invention, reference the following detailed description, taken in connection with the accompanying drawings in which.

DETAILED DESCRIPTION

Figure 1:
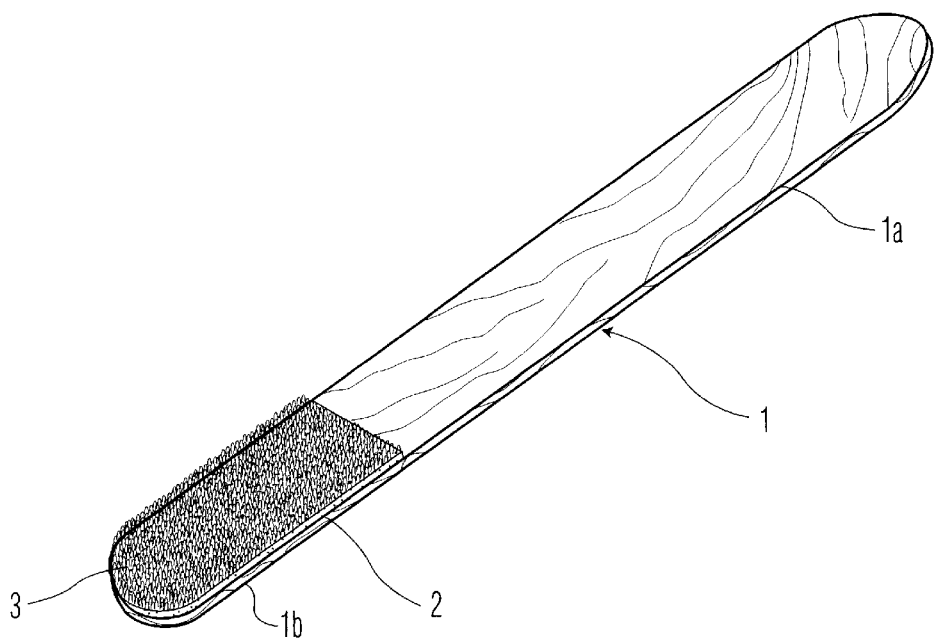
FIG. 1 is a perspective view showing an embodiment of a tongue cleaner in accordance with the present invention.
Figure 3:
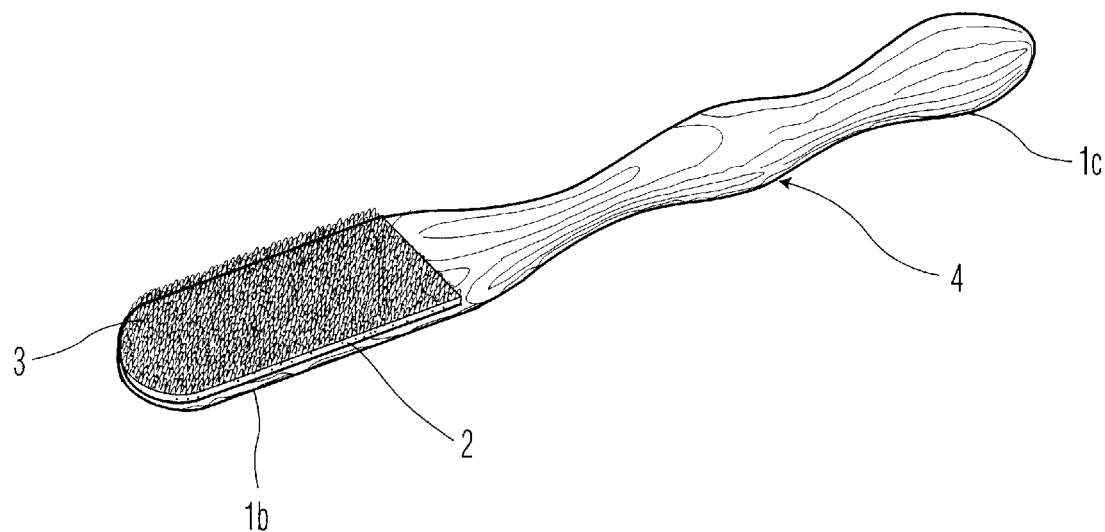
FIG. 3 is a perspective showing another embodiment of a tongue cleaner of the present invention, having an alternative handle design.
Figure 4:
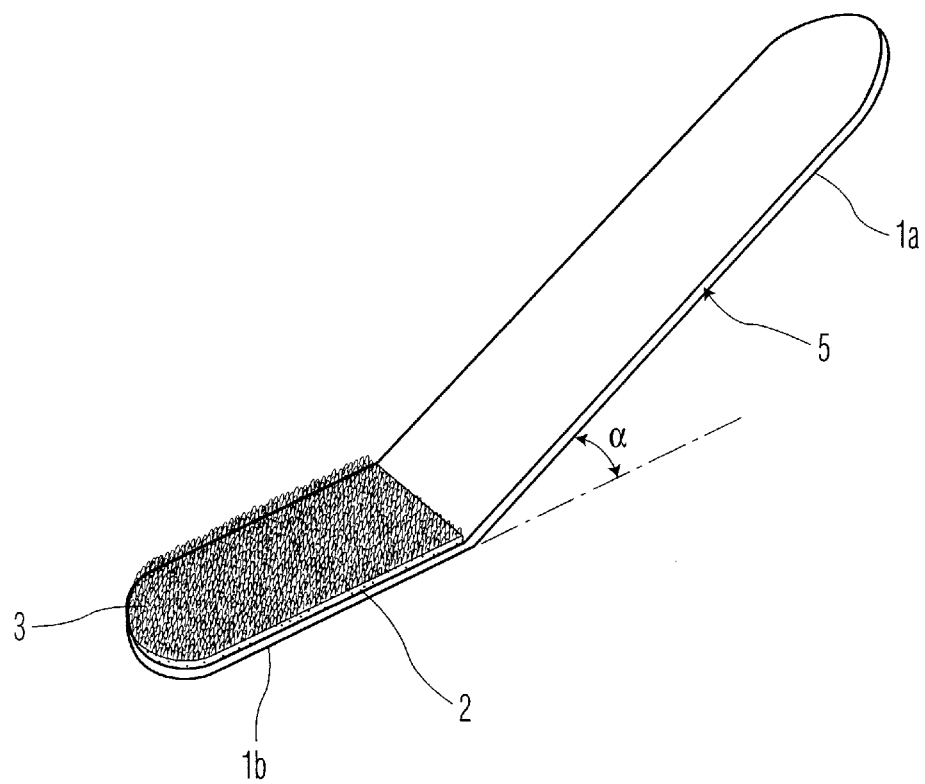
FIG. 4 is a perspective showing another embodiment of a tongue cleaner of the present invention, having the handle raised from the plane in which the head lies.

Reference is made to FIG. 1, wherein a first embodiment of the tongue cleaner of the present invention is shown generally as 1; including a flat, elongated member, of wood, such as a wooden tongue depressor, or a molded plastic tongue depressor, of a moldable plastic material, such as polypropylene. The elongated member functions as both a handle, 1a, for gripping and as a head having a flattened portion or platform, 1b, to maintain the backing tape, 2, and the loop pile, 3, thereon. FIG. 3 is a second embodiment, wherein the end of the elongated member opposite the head, 1b, forms a handle, 1c, having contours to facilitate grasping in the hand. FIG. 4 is a third embodiment, wherein the handle, 1a, is raised from the plane of the head, 1b, by an angle, α, of from 5 to 20 degrees and preferably of from 12 to 15 degrees; this positioning of the head in relationship to the handle allows the head to remain clear of the throat when it is applied to the posterior of the tongue, to avoid the gag reflex, which occurs when the upper portion of the throat is contacted.

Figure 2:
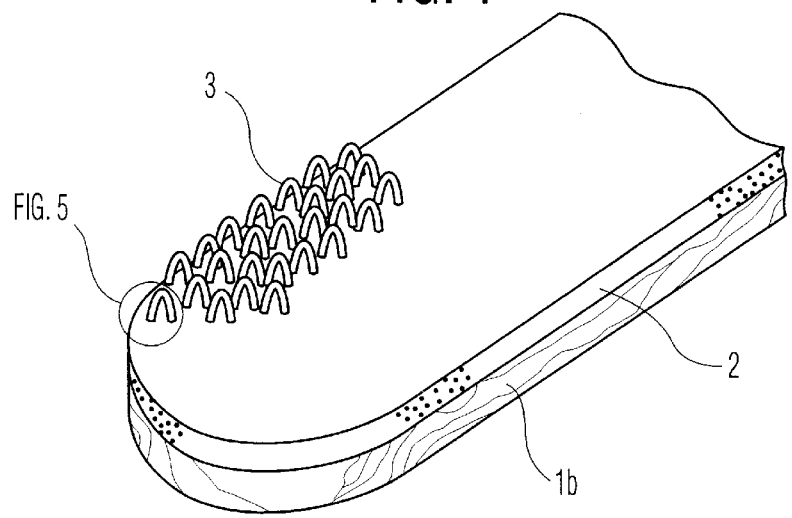
FIG. 2 is an enlarged view of a section of FIG. 1, showing the end of the tongue cleaner upon which the backing tape is attached (i.e. the head), with a fragmentary section of the multifilament yarn bundles which form the loop pile.
Figure 5:
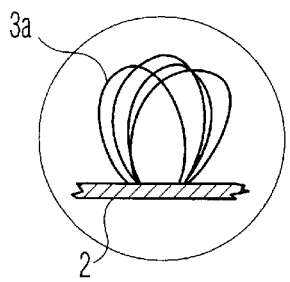
FIG. 5 is an enlargement of a multifilament yarn bundle, with the monofilament loops therein separated.

The multifilament yarn is from about 0.1 mm to about 0.25 mm diameter, preferably from about 0.14 mm to about 0.17 mm in diameter with at least 3, preferably 4 or 5 monofilament loops per bundle; each monofilament being from about 0.03 mm to about 0.045 mm in diameter. The multifilament yarn bundles, 3, shown in FIG. 2, are enlarged in FIG. 5 to show the separated monofilaments, 3a, therein. The density of the loop bundles on the backing tape varies from about 120 bundles per $cm^2$ to about 160 bundles per $cm^2$. The loops are raised from about 0.7 mm to about 1.4 mm, preferably about 0.8 mm to about 1.2 mm in height above the backing tape.

The multifilament yarn bundles, 3, are part of a triple weave, in the same way as astrakhan fabric, preferably of a polyamide yarn, such as nylon or other heat settable, thermoplastic, material. Production of such a triple weave, a woven base having woven therein raised multifilament bundles, to form the loop pile, is known in the art as disclosed in U.S. Pat. No. 3,009,235 and 3,387,345, which are incorporated herein by reference. As disclosed within U.S. Pat. No. 3,009,235, the loops are formed by passing the multifilament yarn over a bar or lancet disposed parallel to direction of the weave of the multifilament yarn within the woven base, the lancet having a first portion of reduced cross-section on which the loops are formed, followed by a progressively enlarging cross-section to tension the loop to the desired oval cross-section. After the weaving is complete, the multifilament yarn bundles are brushed to provoke a separation of each monofilament loop from the others within each bundle. The separated monofilament loops are fixed or stabilized by heat setting or impregnation of the fabric, for example by adhesive products, or both.

The backing tape, 2, is composed of the woven base of the triple weave, which is coated with an adhesive on one side; the multifilament yarn extending from the other side. The woven base is preferably woven of 6.5 mil monofilament or multifilament nylon thread or yarn. A polymeric slip sheet or similar non-sticking material may be used to protect the adhesive coated backing tape, until the backing tape is applied and bonded to the flattened head portion of the elongated member, 1b. The adhesive used must be a non-toxic food-grade adhesive; such a nontoxic adhesive is preferably an acrylic adhesive, such as Spectrum 0172, available from the Velcro Group Corporation, Manchester, N.H. 03108.

A commercially available nylon multifilament loop pile tape for application to the flattened head portion of the elongated member is Loop 1000, Cat. No. 181007 from Velcro Group Corporation, Manchester, N.H. 03108.

The following example is further illustrative of the present invention, but it is understood that the invention is not limited thereto.

EXAMPLE

The cleaning efficacy of a loop pile tongue cleaning device of the present invention was demonstrated by determining the weight of wet debris, bacteria and plaque removed by a series of 3 parallel scrapings covering the upper surface of the tongue, from the posterior to the anterior tip of the tongue. The particular loop pile tongue cleaner used was comprised of a 19 mm wide by 143 mm long polypropylene tongue depressor, having a 19 mm wide by 15 mm long segment of nylon loop pile, Loop 1000, affixed thereto. The nylon loop pile used had a filament bundle density of about 140 bundles per $cm^2$ of the backing tape, and loops which on average were raised about 1.0 mm in height above the backing tape. The weight of material removed from the tongue was determined by the difference in the weight of the tongue cleaning device before and after the series of scrapings, the result is recorded in Table I, below.

For comparison, the experimental procedure was repeated on successive days using a nylon hook brush tongue cleaner, about 22.6 mm in width and 30.5 mm in length, similar to that disclosed in U.S. Pat. No. 3,943,592 and using a conventional, rigid plastic, inverted U-shaped tongue scraping blade having a 12.7 mm radius of curvature within the arcuate portion of the U and about 70 mm parallel sides descending therefrom, similar to the shape of the tongue scrapper disclosed in U.S. Pat. No. 5,569,278. The weight of material removed by these comparative devices is also recorded in Table I, below.

TABLE I

Efficacy of Tongue Cleaners

| Device | Weight of Material Removed (in grams) | % Additional Weight of Material Removed vs. Conventional Inverted U-Shaped Blade |
|---|---|---|
| Conventional Inverted U-Shaped Blade | 0.007 | — |
| Hook Brush | 0.022 | 214% |
| Flexible Loop Pile | 0.13 | 1,757% |

Referring to Table I, the cleaning efficacy of the flexible loop pile tongue cleaner of the present invention was unexpectedly and significantly better than that of the comparative cleaner/scrapers. Further, the flexible loop pile tongue cleaner provided a more consumer acceptable, i.e. soft, tongue feel; not harsh as that of the comparative hook brush or conventional blade.

What is claimed is:

1. An effective, absorbent tongue cleaning device that provides a soft tongue feel comprising a rigid elongated member having at one end a flattened head portion to which a backing tape is attached and at the other end a gripping means; the backing tape containing a plurality of flexible multifilament yarn bundles of monofilament closed loops which form a dense, absorbent loop pile.

2. The tongue cleaning device of claim 1, wherein the loop pile has a density from about 120 to about 160 bundles per square cm of the backing tape; each bundle having a plurality of monofilament loops of from about 0.3 to about 0.45 mm in diameter; the loop pile being from about 0.7 mm to about 1.4 mm in height above the backing tape.

3. The tongue cleaning device of claim 1, wherein the gripping means may be a flat, generally cylindrical or contoured handle to provide ease in holding.

4. The tongue cleaning device of claim 1, wherein the gripping means is a handle, which is raised at an angle of from 5 to 20 degrees from the plane of the flattened head portion.

5. The tongue cleaning device of claim 1, wherein the multifilament yarn is nylon.

6. The tongue cleaning device of claim 1, wherein each multifilament yarn bundle has at least 3 monofilament loops.

7. The tongue cleaning device of claim 1, wherein each bundle has 4 monofilament loops.

8. A method of tongue cleaning comprising applying and scrapping across the surface of a tongue a cleaning device comprising a rigid elongated member having at one end a flattened head portion to which a backing tape is attached and at the other end a gripping means; the backing tape containing a plurality of flexible multifilament yarn bundles of monofilament closed loops which form a dense, absorbent loop pile.

9. The tongue cleaning method of claim 8, wherein the loop pile has a density of from about 120 to about 160 bundles per square cm of the backing tape, each bundle having a plurality of monofilament loops of from about 0.3 to about 0.45 mm in diameter, the pile being from about 0.7 mm to about 1.4 mm in height above the backing tape; wherein the method enhances the absorption and removal of wet debris, bacteria and plaque from the surface of the tongue, while providing a soft tongue feel.

10. The tongue cleaning method of claim 8, wherein the gripping means may be a flat, generally cylindrical or contoured handle to provide ease in holding.

11. The tongue cleaning method of claim 8, wherein the gripping means is a handle, which is raised at an angle of from 5 to 20 degrees from the plane of the flattened head portion.

12. The tongue cleaning method of claim 8, wherein the multifilament yarn is nylon.

13. The tongue cleaning device of claim 8, wherein each multifilament yarn bundle has at least 3 monofilament loops.

14. The tongue cleaning device of claim 8, wherein each multifilament yarn bundle has 4 monofilament loops.

* * * * *